United States Patent [19]
Sauer

[11] Patent Number: 5,902,297

[45] Date of Patent: *May 11, 1999

[54] ABSORBENT ARTICLE HAVING A COLLECTION CONDUIT

[75] Inventor: Barbara Oakley Sauer, Fremont, Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/671,564

[22] Filed: Jun. 27, 1996

[51] Int. Cl.⁶ .................................................. A61F 13/15
[52] U.S. Cl. ..................................... 604/385.1; 604/386
[58] Field of Search ................................ 604/385.1, 369, 604/386, 389–391, 393, 394, 396, 358

[56] References Cited

U.S. PATENT DOCUMENTS

| | | |
|---|---|---|
| 810,122 | 1/1906 | Green . |
| 810,123 | 1/1906 | Green . |
| 810,125 | 1/1906 | Green . |
| 810,130 | 1/1906 | Green . |
| 4,257,418 | 3/1981 | Hessner . |
| 4,662,877 | 5/1987 | Williams . |
| 4,681,577 | 7/1987 | Stern et al. . |
| 4,762,521 | 8/1988 | Roessler et al. . |
| 4,778,459 | 10/1988 | Fuisz ...................................... 604/378 |
| 4,795,453 | 1/1989 | Wolfe ..................................... 604/385.1 |
| 4,798,603 | 1/1989 | Meyer et al. ........................... 604/378 |
| 4,892,536 | 1/1990 | DesMarais et al. .................. 604/385.2 |
| 4,950,262 | 8/1990 | Takagi ................................... 604/385.1 |
| 4,990,147 | 2/1991 | Freeland ............................... 604/385.2 |
| 5,062,840 | 11/1991 | Holt et al. ............................. 604/385.1 |
| 5,169,394 | 12/1992 | Jean ...................................... 604/385.1 |
| 5,171,236 | 12/1992 | Dreier et al. .......................... 604/369 |
| 5,176,668 | 1/1993 | Bernardin .............................. 604/368 |
| 5,176,672 | 1/1993 | Bruemmer et al. ................... 604/385.1 |
| 5,192,606 | 3/1993 | Proxmire et al. ...................... 428/284 |
| 5,207,663 | 5/1993 | McQueen ............................. 604/385.1 |
| 5,269,775 | 12/1993 | Freeland et al. ...................... 604/385.2 |
| 5,281,208 | 1/1994 | Thompson et al. .................... 604/378 |
| 5,300,053 | 4/1994 | Genaro ................................... 604/378 |
| 5,304,159 | 4/1994 | Tanji et al. ............................ 604/385.2 |

(List continued on next page.)

FOREIGN PATENT DOCUMENTS

| | | |
|---|---|---|
| 0692231A1 | 1/1996 | European Pat. Off. . |
| 6237953 | 8/1994 | Japan ................................. 604/385.1 |
| 949179 | 11/1994 | South Africa . |
| 949262 | 11/1994 | South Africa . |
| 2176388 | 12/1986 | United Kingdom ................ 604/385.1 |
| 2 284 831 | 6/1995 | United Kingdom ............ A61F 13/15 |
| 2284537 | 6/1995 | United Kingdom . |
| 2284538 | 6/1995 | United Kingdom . |
| 2284550 | 6/1995 | United Kingdom . |
| 2287393 | 9/1995 | United Kingdom . |
| WO 93/25170 A1 | 12/1993 | WIPO ............................ A61F 13/15 |
| 96/01609 | 1/1996 | WIPO . |
| WO 96/07381 A3 | 3/1996 | WIPO ............................ A61F 13/15 |
| WO 96/20674 A1 | 7/1996 | WIPO ............................ A61F 13/15 |
| WO 96/34589 A3 | 11/1996 | WIPO ............................ A61F 13/15 |

*Primary Examiner*—Mark O. Polutta
*Attorney, Agent, or Firm*—Jeffrey B. Curtin

[57] ABSTRACT

An absorbent article includes a conduit means which is located on a body facing surface along a longitudinal centerline of said absorbent article for collecting and transporting fecal material. The conduit means is configured to maintain at least partial contact with a gluteal fold region between a wearer's buttocks when in use. The conduit means includes an inner surface which defines an internal void volume for containing the fecal material and at least one opening through the inner surface to allow the fecal material to pass into the internal void volume. The conduit means also defines a relatively high resistance to compression and level of flexibility for improved performance.

38 Claims, 6 Drawing Sheets

OTHER PUBLICATIONS

| | | | |
|---|---|---|---|
| 5,304,160 | 4/1994 | Igaue et al. | 604/385.2 |
| 5,306,266 | 4/1994 | Freeland | 604/385.1 |
| 5,324,278 | 6/1994 | Visscher et al. | 604/385.1 |
| 5,330,459 | 7/1994 | Lavon et al. | 604/385.1 |
| 5,330,598 | 7/1994 | Erdman et al. | 156/164 |
| 5,344,516 | 9/1994 | Tanji et al. | 156/164 |
| 5,356,405 | 10/1994 | Thompson et al. | 604/384 |
| 5,366,453 | 11/1994 | Zehner et al. | 604/385.2 |
| 5,391,160 | 2/1995 | Runeman et al. | 604/378 |
| 5,409,476 | 4/1995 | Coates | 604/391 |
| 5,417,680 | 5/1995 | Kimura et al. | 604/385.2 |
| 5,439,458 | 8/1995 | Noel et al. | 604/378 |
| 5,439,459 | 8/1995 | Tanji et al. | 604/385.2 |
| 5,451,442 | 9/1995 | Pieniak et al. | 428/54 |
| 5,462,539 | 10/1995 | Herman et al. | 604/385.1 |
| 5,509,915 | 4/1996 | Hanson et al. | 604/378 |

ABSORBENT ARTICLE HAVING A COLLECTION CONDUIT

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which are configured to collect and contain fecal material and avoid leakage.

2. Description of the Related Art

Conventional absorbent articles, such as disposable diapers, employ absorbent materials located between a liquid pervious topsheet and a liquid impermeable backsheet to absorb body exudates. Such conventional absorbent articles have also typically included elasticized waistbands and leg cuffs to help reduce the leakage of body exudates.

However, many of such conventional absorbent articles have not been completely satisfactory. For example, many conventional absorbent articles have not completely contained the body exudates within the article during use thereby undesirably resulting in leakage which has soiled the clothes of the wearer. This leakage problem has been particularly evident in the crotch area of such absorbent articles when runny or watery fecal material has been excreted by the wearer during use. Typically, the crotch area of such articles is relatively narrow to provide optimum fit between the legs of the wearer. The narrow crotch and corresponding low amount of absorbent material in the crotch area has adversely affected the ability of the article to absorb and contain all of the body exudates which are typically discharged in this area thereby resulting in leaks. Such problems are magnified when the wearer is particularly active and continually exerts pressure on the crotch area of the article. The leakage problem has also occurred because the excreted fecal material has had an affinity for the skin. As a result, such fecal material has traveled along the skin of the wearer and has not been sufficiently contained and controlled within the absorbent articles.

Some conventional absorbent articles have included elasticized containment or barrier flaps at the leg sections of the article to reduce such leaks. However, such containment flaps have not completely eliminated all leakage from the article. For example, exudates such as runny fecal material have remained on and been transferred along the skin of the wearer until they escape through small openings between the containment flaps and the body of the wearer. Such openings between the body of the wearer and the containment flaps have been caused by improper fit of the article about the wearer and the movements of the wearer during use.

As a result, although such containment flaps have improved the performance of such articles, there remains a need to further reduce the number of leaks and, in particular, the number of leaks of fecal material from such absorbent articles.

SUMMARY OF THE INVENTION

In response to the difficulties and problems discussed above, a new disposable absorbent article which has a collection conduit for collecting and containing fecal material has been discovered.

As used herein, the term "flexibility" refers to the flexibility of a material determined according to the Flexibility Test set forth below.

As used herein, the term "compression resistance" refers to the compression resistance value determined according to the Compression Resistance Test set forth below.

In one aspect, the present invention relates to a disposable absorbent article which comprises a conduit means. The conduit means is located on a body facing surface along a longitudinal centerline of the absorbent article for collecting and transporting fecal material. The conduit means is configured to maintain at least partial contact with a gluteal fold region between a wearer's buttocks when in use. The conduit means includes an exterior wall which defines an internal duct and at least one opening through the exterior wall into the internal duct for collecting and transporting the fecal material. Each opening in the external wall is configured to define an area of at least about 0.8 square centimeters. In a particular embodiment, the conduit means defines an internal void volume of at least about 5.0 cubic centimeters for containing said fecal material and a compression resistance of at least about 25 percent.

In another aspect, the present invention relates to an absorbent article having a front waist section, a rear waist section, an intermediate section which interconnects said front and rear waist sections, a pair of longitudinally opposed end edges, and a pair of laterally opposed side edges. The article comprises a) a backsheet layer; b) a liquid permeable topsheet layer which is connected in superposed relation to the backsheet layer; c) an absorbent body which is located between the topsheet layer and the backsheet layer; and d) a collection conduit which is located on the topsheet layer along a longitudinal centerline of the absorbent article. The collection conduit includes an exterior wall which defines an internal duct for collecting and transporting fecal material. In a particular embodiment, at least about 25 percent of the exterior wall of the collection conduit in the target zone remains open to collect and transport the fecal material into the internal duct.

In another particular embodiment, the absorbent article further comprises a waist flap which is located in the rear waist section of the absorbent article. The waist flap defines an attached edge which is attached to the end edge and the side edges of the absorbent article in the rear waist section and a free edge which extends inwardly from the end edge towards the intermediate section of the article. The free edge remains at least partially unattached to the topsheet of the absorbent article to provide a pocket to contain body exudates. The waist flap may extend inwardly over a longitudinal end of the collection conduit.

In yet another aspect, the present invention relates to an absorbent article which comprises a) a backsheet layer; b) a liquid permeable topsheet layer which is connected in superposed relation to the backsheet layer, c) an absorbent body which is located between the topsheet layer and the backsheet layer; and d) a spiral coil which is located on the topsheet layer along a longitudinal centerline of the absorbent article. The spiral coil defines an interior void volume of at least about 5.0 cubic centimeters and a compression resistance of at least about 25 percent for collecting and containing fecal material. In a particular embodiment, the spiral coil defines a flexibility of less than about 20 centimeters and an inner surface having a coefficient of friction of no more than about 1.0.

The various aspects of the present invention can advantageously provide an absorbent article which effectively absorbs and contains body exudates. In particular, the present invention removes and collects exudates such as runny fecal material from the skin of the wearer and transports such exudates to portions of the article where they are more effectively contained. As a result, the absorbent articles of the various aspects of the present invention have reduced leakage when compared to conventional absorbent articles which results in improved consumer preference.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
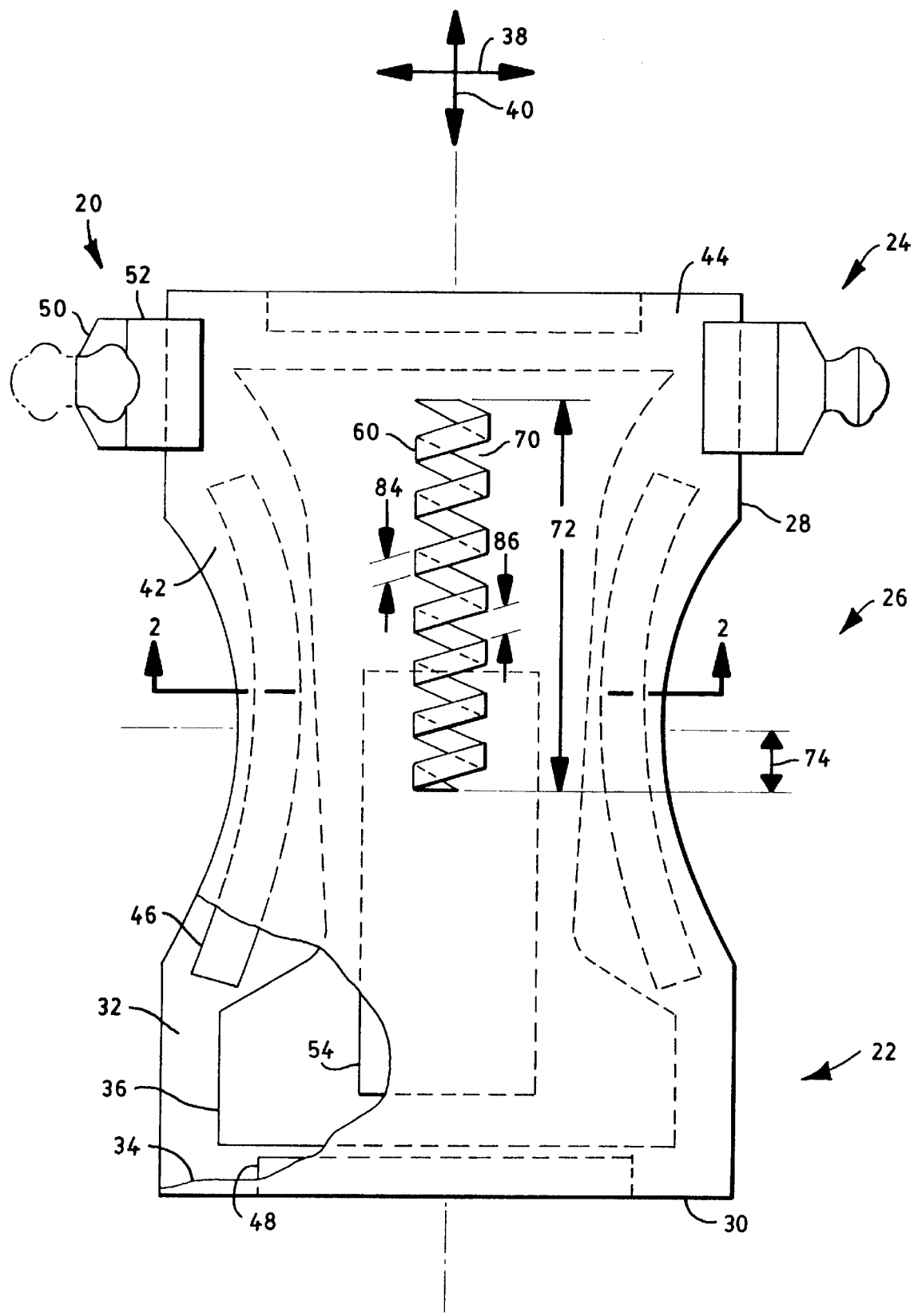
FIG. 1 representatively shows a partially cut away, top plan view of an absorbent article according to one embodiment of the invention.
Figure 2:
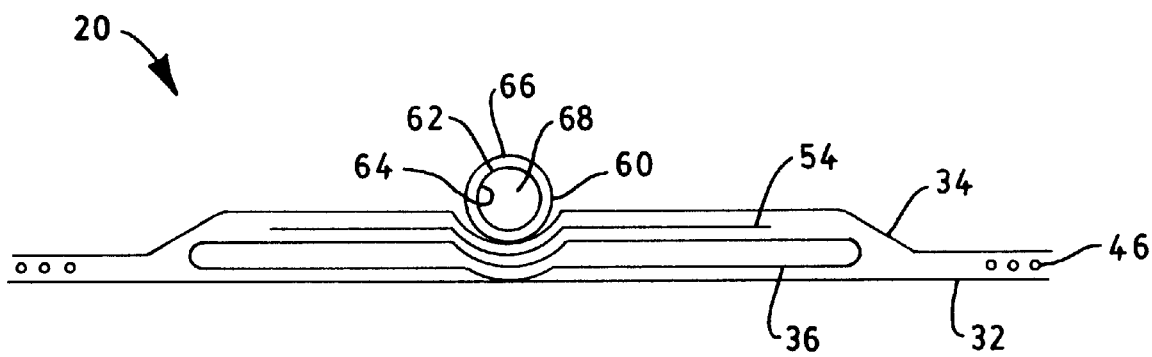
FIG. 2 representatively shows a sectional view of the absorbent article of FIG. 1 taken along line 2—2.
Figure 3:
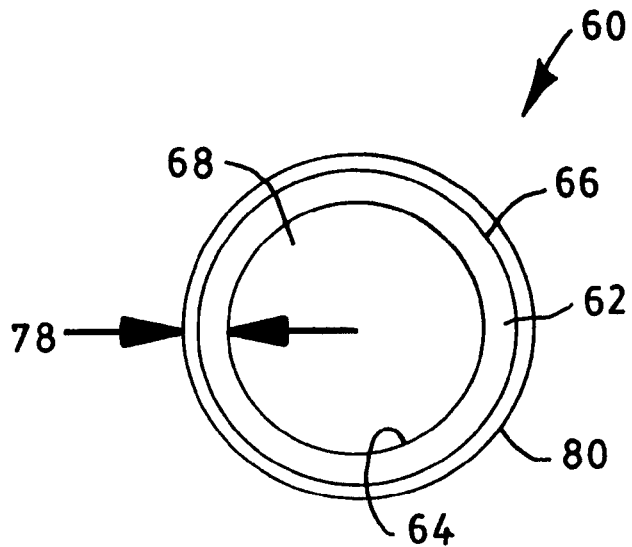
FIG. 3 representatively shows a sectional view of a collection conduit according to one embodiment of the invention.

With reference to FIGS. 1 and 2, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearers crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable backsheet 32, a porous, liquid permeable topsheet 34 positioned in facing relation with the backsheet 32, and an absorbent body 36, such as an absorbent pad, which is located between the backsheet and the topsheet. The diaper 20 also defines a lateral direction 38 and a longitudinal direction 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIGS. 1 and 2, the elastic members 46 and 48 are illustrated in their uncontracted, stretched condition for the purpose of clarity. Alternatively, the diaper 20 may include a pair of separate, elasticized and gathered leg gussets (not shown) which are attached to the diaper along the side margins 42 in at least the intermediate section 26 of the diaper 20 to provide elasticized leg cuffs. Such leg gussets may be configured to extend beyond and bridge across the respective concave portion of the side margins 42.

The diaper 20, as representatively illustrated in FIGS. 1 and 2, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20.

The diaper 20 may also include a pair of elasticized, longitudinally extending containment flaps (not shown) which are configured to maintain an upright, perpendicular arrangement in at least the intermediate section 26 of the diaper 20 to serve as an additional barrier to the lateral flow of body exudates. The diaper 20 may further include a surge management layer 54 positioned between the topsheet 34 and the absorbent body 36 which is configured to efficiently hold and distribute liquid exudates to the absorbent body 36. The surge management layer 54 can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20, as representatively illustrated in FIGS. 1 and 2, further includes at least one collection conduit 60 which is located on the bodyfacing surface of the topsheet 34. For example, the diaper 20 may include from 1 to about 3 collection conduits which are longitudinally aligned in the diaper 20. The collection conduit 60 is configured to collect and transport fecal material to regions of the diaper 20 such as the rear waist section 24 to more effectively contain such material within the diaper 20.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bemardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference to the extent they are consistent herewith. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the topsheet 34 and backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper article by employing the above-identified attachment mechanisms.

The backsheet 32 of the diaper 20, as representatively illustrated in FIGS. 1 and 2, may suitably be composed of a material which is either liquid permeable or liquid impermeable. It is generally preferred that the backsheet 32 be formed from a material which is substantially impermeable to liquids. For example, a typical backsheet can be manufactured from a thin plastic film or other flexible liquid-impermeable material. For example, the backsheet 32 may be formed from a polyethylene film having a thickness of from about 0.012 millimeter (0.5 mil) to about 0.051 millimeter (2.0 mils). If it is desired to present the backsheet with a more clothlike feeling, the backsheet 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 32 may be formed of a woven or nonwoven fibrous web layer which has been totally or partially constructed or treated to impart a desired level of liquid impermeability to selected regions that are adjacent or proximate the absorbent body 36. Still further, the backsheet 32 may optionally be composed of a micro-porous "breathable" material which permits vapors to escape from the absorbent body 36 while still preventing liquid exudates from passing through the backsheet 32. The backsheet 32 typically provides the outer cover of the diaper 20. The backsheet 32 can also be embossed or otherwise provided with a matte finish to provide a more aesthetically pleasing appearance.

The topsheet 34, as representatively illustrated in FIGS. 1 and 2, suitably presents a bodyfacing surface which is compliant, soft feeling, and nonirritating to the wearer's skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearers skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation Triton X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The collection conduit 60, as representatively illustrated in FIGS. 1 and 2, is configured to help reduce leaks by collecting and transporting fecal material from the target zone of the diaper 20 to regions of the diaper 20 which have an increased capability of absorbing and containing such material. As used herein, the term "target zone" refers to that portion of the diaper 20 which is configured to directly receive the insult of fecal exudates from the wearer and generally is located in the crotch portion of the diaper 20. In particular, the target zone may extend from about 5 to about 10 centimeters in length with about one third of it's length extending longitudinally from the centerline of the diaper towards the front waist section 22 of the diaper 20 and the remainder extending longitudinally towards the rear waist section 24 of the diaper 20. Since the crotch portion of the diaper 20 is typically the narrowest portion of the diaper 20, it generally does not have enough absorbent capacity and area to absorb and contain all of the body exudates during heavy insults. In addition, in use, the crotch portion of the diaper 20 may have forces exerted upon it which may tend to force exudates and, in particular, fecal material out of the diaper. Accordingly, the collection conduit 60 of the present invention is configured to transport such exudates to other portions of the diaper 20 to provide better containment and reduce leaks.

In the illustrated embodiments, a single collection conduit 60 is located along the longitudinal centerline 40 of the diaper 20 and is configured to maintain at least partial contact with the gluteal fold region of the wearer when in use. As used herein, the term "gluteal fold" is intended to mean the somewhat void region between the wearers buttocks. The collection conduit 60 is configured to ride in the gluteal fold region during use to maintain close contact with the anal region of the wearer to collect and transport substantially all of the fecal exudates. When located in the gluteal fold, the collection conduit 60 is not subjected to all of the compressive forces which are exerted by the wearer and, as a result, remains more open and causes limited redmarking and irritation of the wearer. The desired location of the collection conduit 60 in the gluteal fold also tends to prevent the void space between the buttocks of the wearer from pinching together thereby avoiding the explosive flow of fecal material up the back of the diaper which may result from such pinching. The collection conduit 60 further tends to provide a scraping and entrapment effect during use to help remove and collect fecal material from the skin of the wearer.

In general, the collection conduit 60 is positioned on the bodyfacing surface of the topsheet 34 of the diaper 20. The collection conduit 60 may remain substantially unattached to the topsheet 34 or may be attached to the topsheet 34 using conventional means described above such as adhesive. In one embodiment of the present invention, the collection conduit 60 may be held in place by one or more strips of a material such as a nonwoven material or foam material which extend over the bodyfacing surface of the collection conduit 60 and which may be attached to the topsheet 34 of the diaper 20 using adhesive. Desirably, the strips of material do not cover any of the openings 70 in the conduit 60. The strips of material may be provided by a material which is relatively soft to provide a cushion between the conduit 60 and the body of the wearer to prevent irritation and redmarking. Such strips may also be somewhat absorbent in nature to help absorb and liquid exudates.

Typically, the collection conduit 60 is located in the intermediate section 26 of the diaper 20 and may or may not extend into the front or rear waist sections 22 and 24. The collection conduit 60 may or may not be located in the target zone depending upon whether it is intended to be in close proximity with the anus of the wearer to collect and transport the fecal material into the other portions of the diaper 20. Desirably, the collection conduit 60 is at least partially located in the target zone for improved performance. In a particular embodiment as illustrated in FIG. 1, a longitudinal end of the collection conduit 60 is located a distance 74 from the centerline of the diaper 20 towards the front section 22 of the diaper 20 and the conduit 60 extends longitudinally into the rear waist section 24 of the diaper. For example, the longitudinal end of the collection conduit 60 may be located a distance 74 of from about 0 to about 5.0 centimeters and desirably from about 1 to about 3 centimeters from the centerline towards the front waist section 22 of the diaper 20. Such a configuration is desirable to allow the collection conduit 60 to collect the fecal material in the target zone or intermediate section 26 of the diaper 20 and transport it into the rear waist section of the diaper. Desirably, the collection conduit 60 is configured to be positioned just behind the genitals of the wearer to avoid irritation. Such a location is particularly important when the diaper 20 is intended to be worn by males. The opposite end of the conduit 60 which is located in the rear waist section of the diaper 20 may remain open such that fecal material can exit the conduit 60 in a location of the diaper 20 which can more readily contain it. Alternatively, the end of the conduit extending into the rear waist section may be plugged such that fecal material can not exit the conduit 60.

Figure 4:
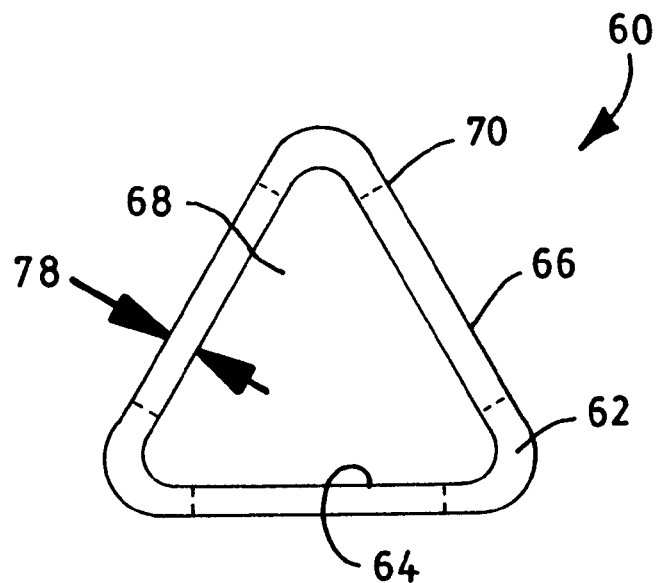
FIG. 4 representatively shows a sectional view of a collection conduit according to another embodiment of the invention.
Figure 5:
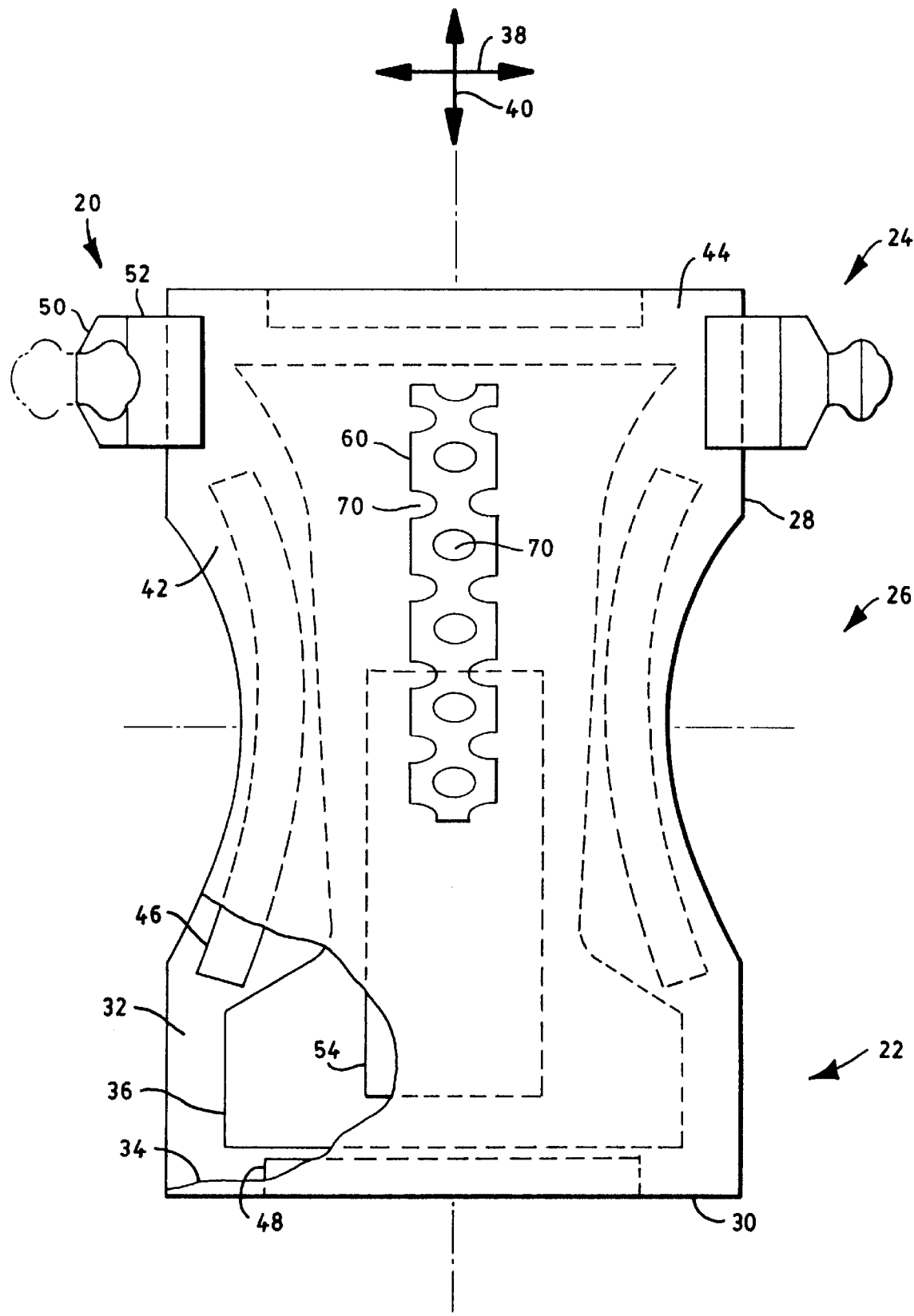
FIG. 5 representatively shows a partially cut away, top plan view of an absorbent article according to another embodiment of the invention.

The collection conduit 60 may have any shape which provides the desired collection and transport of the fecal material. For example, as representatively illustrated in FIGS. 1 and 2, the collection conduit may be in the form of a spiral coil. Alternatively, as representatively illustrated in FIGS. 3–6, the collection conduit 60 may have a tubular or triangular configuration. Shapes such as the triangular shape representatively illustrated in FIG. 4, may more readily conform to the gluteal fold region between the wearer buttocks. Another shape suitable for the collection conduit 60 is a semi-triangular shaped with curved sides to provide improved fit between the buttocks of the wearer. Alternatively, the collection conduit need not be completely enclosed. For example, the conduit 60 may be V-shaped C-shaped with the open end of the V or C being positioned to face the topsheet of the diaper 20.

As representatively illustrated in FIGS. 1–6, the collection conduit 60 defines an exterior wall 62, an inner surface 64, an outer surface 66 and a thickness 78. The inner surface 64 of the collection conduit 60 defines an internal duct 68 which provides void volume for collecting and transporting fecal material. The collection conduit 60 further defines at least one opening 70 through the exterior wall 62 which is configured to allow the fecal material to pass through the exterior wall and into the internal duct 68. The opening 70 is located on a portion of the exterior wall which is not in contact with the topsheet 34 of the diaper 20 such that it remains clear in use to collect the fecal material. As representatively illustrated in FIG. 6, when the collection conduit 60 is completely enclosed, the conduit 60 may further define a plurality of holes 82 through the portion of the exterior wall 62 which is in contact with the topsheet 34 to allow any liquids to pass out of the conduit 60 into the absorbent body 36 of the diaper 20.

The internal duct 68 of the collection conduit 60 is configured to contain and transport the fecal material. The size of the internal duct 68 can vary depending upon the intended use and loading of the diaper 20. However, in general it is desirable that the internal duct 68 of the collection conduit 60 provide at least about 5.0, more desirably at least about 15.0, and most desirably at least about 20.0 cubic centimeters of void volume to contain the fecal material. To provide such void 30 volume, the internal duct 68 may extend substantially along the entire length 72 of the collection conduit. For example, the length 72 of the collection conduit 60 and the corresponding length of the internal duct 68 may be from about 10 to about 80 percent, and desirably from about 35 to about 60 percent of the length of the diaper 20. On a diaper article intended to be worn by a medium-sized infant, the length 72 of the collection conduit 60 may be at least about 5.0 centimeters and desirably from about 5.0 to about 30.0 centimeters. The internal duct 68 of the collection conduit 60 may also define an average cross-sectional area of at least about 0.4 square centimeters and desirably at least about 1.0 square centimeters to provide the desired void volume.

The collection conduit 60 is also configured to maintain the void volume in the internal duct 68 during use to contain the fecal material. For example, it is desirable that the collection conduit 60 be capable of resisting any z-directional compressive forces which may be exerted by the wearer during use. Since the collection conduit 60 is located in or along the gluteal fold, the compressive forces exerted by the wearer are minimized because the collection conduit 60 tends to gently press apart the buttocks of the wearer and locate itself between the buttocks. However, even though such compressional forces may be low, it is still desirable that the collection conduit 60 be compression resistant. Accordingly, in a particular embodiment, the collection conduit 60 defines a z-directional compression resistance of at least about 25 percent, desirably at least about 50 percent, and more desirably at least about 70 percent. For example, the collection conduit 60 may have a compression resistance of from about 25 to about 90 percent. When the collection conduit has a compression resistance less than the values set forth above, the collection conduit may collapse during usage which adversely affects the ability of the conduit to collect, contain and transport fecal material. Whereas, if the compression resistance of the collection conduit is too high, the collection conduit may cause undesired redmarking and irritation of the skin of the wearer. Due to the location of the collection conduit between the buttocks, such redmarking can be kept to a minimum even with a highly compression resistant material.

It is also desirable that the collection conduit 60 be flexible such that it readily conforms to the shape and contours of the gluteal fold region between the wearers buttocks. Accordingly, in a particular embodiment, the collection conduit 60 defines a flexibility of less than about 20 centimeters and desirably less than about 15 centimeters. If the flexibility of the collection conduit is too low, the collection conduit may not effectively ride in the gluteal fold region along the body of the wearer and may cause undesired redmarking and irritation of the skin of the wearer.

The flexibility of the collection conduit 60 also provides an important role in removing fecal material from the skin of the wearer. As the collection conduit bends and flexes, the openings through the wall of the conduit expand and contract thereby providing a scraping action along the skin of the wearer and an entrapment action to remove and collect any fecal material adhered to the skin.

The inner surface 64 of the exterior wall 62 of the collection conduit 60 is configured to define the internal duct 68 which is intended to contain and transport the fecal material. To improve the transport of the fecal material along the internal duct 68, it is desirable that the inner surface 64 of the exterior wall 62 be relatively smooth and slippery such that the fecal material readily moves along it without adhering to it. In a particular embodiment, it is desirable that the inner surface 64 have a coefficient of friction of no more than about 1.0 and desirably no more than about 0.5 to provide improved transport of the fecal material. When the coefficient of friction of the inner surface 64 is too high, the fecal material may tend to adhere to the surface and block the internal duct 68. Thus, when the coefficient of friction of the inner surface is too high, the overall capacity of the collection conduit may not be completely utilized and additional fecal material may be prevented from entering the conduit.

When the collection conduit 60 is located in the target zone of the diaper 20, the collection conduit 60 may have any number of openings 70 through the exterior wall 62 to provide the desired collection of fecal material. For example, the exterior wall 62 of the collection conduit 60 may have from 1 to about 10 openings therethrough into the duct. The openings 70 are generally configured to be located in the target zone of the diaper 20 to readily accept the fecal material. Desirably, the openings 70 in the collection conduit 60 are positioned such that, in use, they are located in the gluteal fold and in close proximity to the anus of the wearer. For example, the collection conduit 60 may have about 1 opening per centimeter of length in the target zone. The openings 70 are further configured such that in use they are not blocked or covered by the topsheet 34 such that they can readily accept and collect the fecal material. For example, the openings 70 may be located on the bodyfacing surface or side surfaces of the collection conduit 60 to collect the fecal material. Applicants have discovered that by having more than 1 opening and desirably a plurality of openings in the collection conduit 60, the location of the openings is not as critical as it may be with just one opening to obtain proper placement of the opening relative to the anus of the wearer. Moreover, if one of the openings plugs during use, the adjacent openings can readily receive and collect any excess fecal material.

The openings 70 in the exterior wall 62 of the collection conduit 60 may have any desired shape which provides the collection of fecal material. For example, the openings 70 may be circular, elliptical, square, triangular, rectangular, and the like, or may be continuous. In a particular embodiment, as representatively illustrated in FIG. 1, the collection conduit 60 may be a spiral coil which defines a coil width 84 and a continuous coil spacing 86 which provides the opening 70 through the exterior wall 62. Alternatively, as representatively illustrated in FIGS. 5 and 6, the openings 70 may be circular or elliptical in shape.

Applicants have discovered that the size of the openings 70 and the corresponding percentage of the area of the exterior wall which remains open is important to provide the desired collection of fecal material while still being able to contain a substantial portion of the fecal material within the internal duct 68 of the collection conduit 60. For example, when the openings are discrete openings, it is desirable that each opening 70 define an area of at least about 0.8 square centimeters, desirably from about 1.0 to about 5.0 square centimeters, and more desirably from about 1.5 to about 3.0 square centimeters for improved performance. Alternatively, when the opening 70 is a continuous strip, such as the spacing 86 defined in the spiral coil in the embodiment illustrated in FIG. 1, it is desirable that the strip or spacing 86 define a width which is from about 0.5 to about 4.0 centimeters and desirably from about 1.0 to about 2.5 centimeters wide to provide improved performance. When the size of the opening 70 is greater than that described above, the opening 70 may adequately collect the fecal material but the fecal material may easily return back through the opening 70 during usage or the body of the wearer may be forced into the opening causing irritation and discomfort. When he size of the opening is smaller than that described above, the fecal material may not readily flow through the opening 70 into the internal duct 68 of the collection conduit 60. Instead, the fecal material may follow the outer surface 66 of the conduit 60 and undesirably result in leakage.

Desirably, the exterior wall 62 of the collection conduit 60 has enough total open area due to the openings 70 to allow all of the fecal material to enter the collection conduit even under heavy insults. For example, it is desirable that the openings 70 through the exterior wall 62 include at least about 25 percent and desirably at least about 50 percent of the area of the outer surface 66 of the exterior wall 62 in the target zone to provide improved collection of the fecal material during heavy insults. Desirably, the openings through the exterior wall 62 provide a total open area of at least about 5.0 square centimeters and more desirably at least about 10.0 square centimeters in the target zone for improved performance. The number of openings in the conduit and the total open area of the conduit outside of the target zone, such as the far end of the conduit in the rear waist section 24 of the diaper 20, may be less than that in the target zone since less fecal material will enter into the conduit and be collected in such areas. The number of openings and total open area of the conduit 60 also increase the flexibility of the conduit.

If the collection conduit 60 is not located in the target zone but instead is located more towards the rear of the diaper 20, the collection conduit 60 may not be required to have openings through the exterior wall as long as the longitudinal end of the conduit nearest the target zone is open. The open end thereby allows fecal material to flow into the conduit such that it can be collected and transported to other portions of the diaper. Such a configuration may be particularly desirable when the collection conduit 60 is used in conjunction with a rear waist flap as described below.

Figure 6:
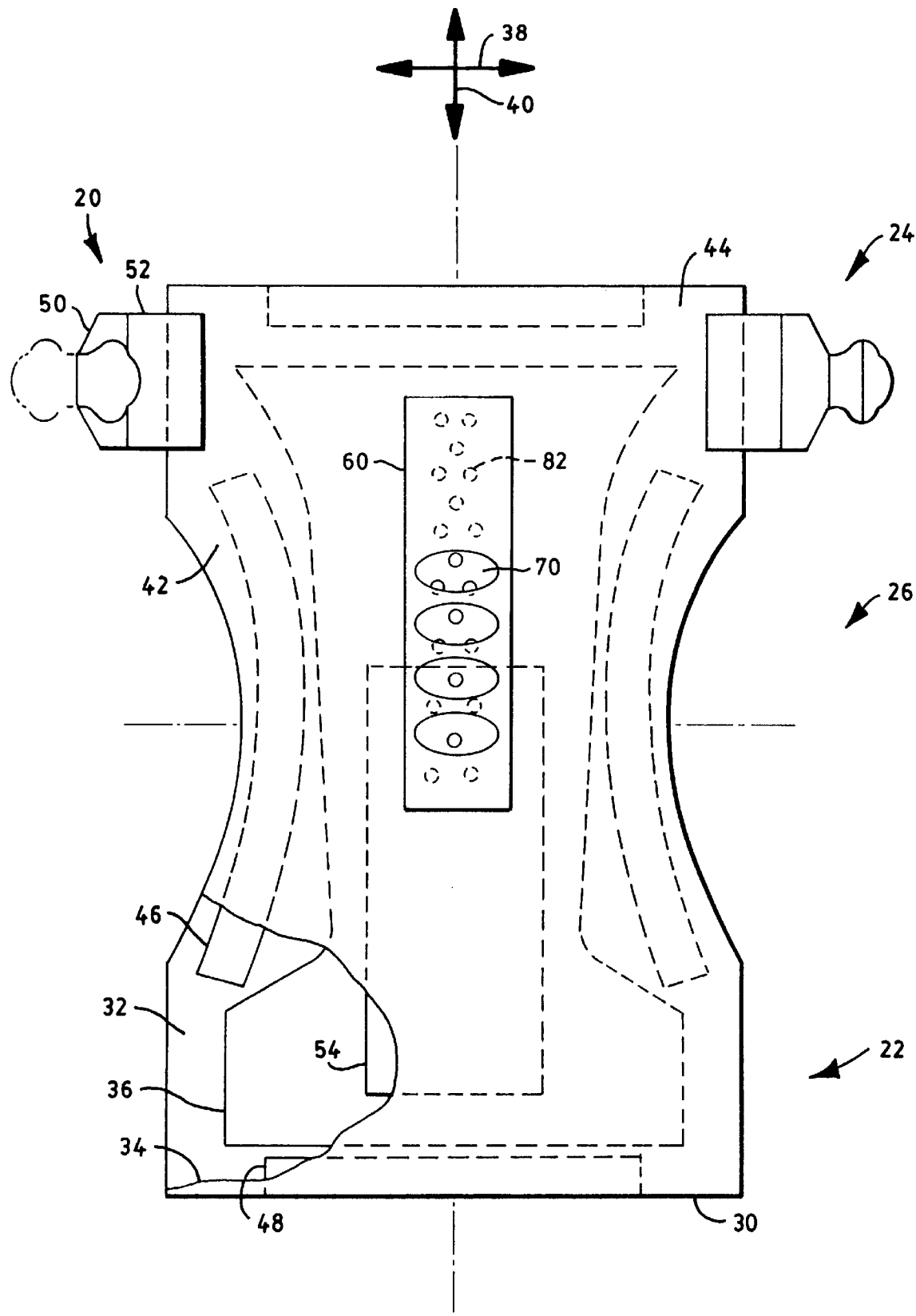
FIG. 6 representatively shows a partially cut away, top plan view of an absorbent article according to another embodiment of the invention.

As representatively illustrated in FIG. 6, the collection conduit 60 may further define a plurality of holes 82 through the portion of the exterior wall 62 which is in contact with the topsheet 34 to allow any liquids to pass out of the conduit 60 into the absorbent body 36 of the diaper 20. For example, the collection conduit 60 may include from about 2 to about 20 holes 82 through the garment facing surface of the exterior wall 62 for improved performance. The holes 82 provide particularly improved results when the fecal material is liquid or runny such as in newborn which are being breast fed. The holes 82 also tend to dewater and reduce the viscosity of the fecal material in the conduit such that it remains inside the conduit for improved performance. Likewise, the holes 82 will allow any urine which enters the conduit 60 to pass into the absorbent body 36.

The collection conduit 60 of the different aspects of the present invention, as representatively illustrated in FIGS.

1–7, may be made from any material which provides the desired levels of compression resistance and flexibility. For example, as representatively illustrated in FIG. 1, the collection conduit may be a spring coil which is manufactured from a TYGON tube material. Desirably each coil of the spring coil is configured to deform slightly in the z-direction when forces are exerted upon it instead of collapsing or folding over which may undesirably reduce the effectiveness of the coil. In a particular embodiment, the spring coil may have an inside diameter of at least about 0.5 centimeters and desirably from about 1.0 to about 2.0 centimeters, a coil width 84 of from about 0.2 to about 0.5 centimeters, and a spacing 86 between each coil of from about 0.3 to about 1.5 centimeters. A particular well suited coil is made from a TYGON tube having an inside diameter of about 1.3 centimeters, an outside diameter of about 1.9 centimeters, and a length of about 17.8 centimeters. The TYGON tube is slit and slightly stretched to provide the coil. Suitable tubes from which the spring coils are manufactured are commercially available from Baxter Diagnostics, a business having offices located in McGraw, Ill. under the trade designation S-50-HL. Another suitable tube is available from Advanced Technology Products Co., a business having offices located in Milford Center, Ohio, under the trade designation 532-30-WH and having an inside diameter of from about 0.2 to about 0.7 centimeters. Alternatively, as representatively illustrated in FIGS. 5 and 6, the collection conduit 60 may include a TYGON tube material as described above which has not been cut into a coil. Alternatively, the collection conduit may be made from other materials such as thermoformed materials or foamed polymers.

Figure 7:
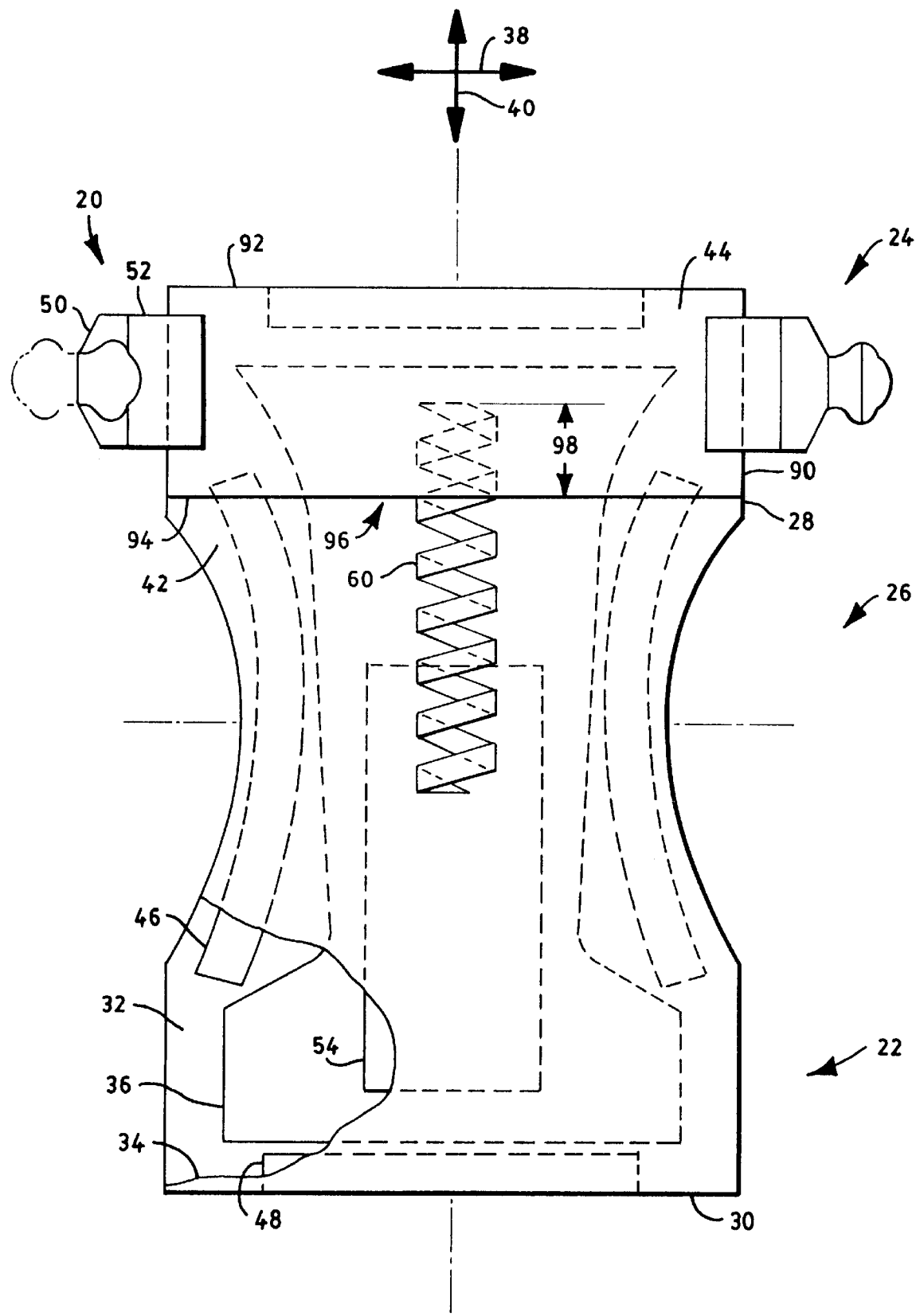
FIG. 7 representatively shows a partially cut away, top plan view of an absorbent article according to yet another embodiment of the invention.

As representatively illustrated in FIG. 7, the diaper 20 of the different aspects of the present invention may further include a rear waist flap 90 which is located on the body-facing side of the bodyfacing side of the diaper 20 in the rear waist section general, the rear waist flap 90 defines an attached edge 92 which is attached to the end edge 30 and said side edges 28 of the diaper 20 in the rear waist section 24. The rear waist flap 90 further defines a free edge 94 which extends inwardly from the end edge 30 of the diaper 20 towards the intermediate section 26 of the diaper 20. The free edge 94 of the rear waist flap 90 is configured to remain at least partially unattached to the topsheet 34 of the diaper 20 to provide a pocket 96 to contain body exudates. To maintain the pocket 96 open during use, the free edge 94 of the waist flap 90 may be rendered elastically contractible by means well known to those skilled in the art. For example, an elastic strand may be adhesively adhered to the free edge 94 in an elongated condition such that when relaxed the elastic strand contracts and gathers the free edge 94 of the waist flap 90.

In a particular embodiment, the rear waist flap 90 may extend inwardly towards the intermediate section 26 and over a longitudinal end of the collection conduit 60. In such a configuration, the collection conduit 60 is configured to transport the fecal material from the target zone or intermediate section 26 of the diaper 20 into the rear waist section 24 and, in particular, into the pocket 96 formed by the rear waist flap 90 where it can be contained. The waist flap 90 may extend inwardly over the collection conduit any distance 98 which provides the desired containment of the fecal material. For example, the free edge 94 of the waist flap 90 may extend inwardly over the collection conduit a distance 98 of at least about 3.0 centimeters and desirably at least about 6.0 centimeters for improved performance. In such a configuration, the collection conduit 60 also acts as a spacer to maintain the free edge 94 of the waist flap 90 in a spaced apart relation from the topsheet 34 of the diaper during use.

The waist flap 90 can be made from many materials well known to those skilled in the art. For example, the waist flap 90 may be made from materials described above as being well suited for the backsheet 32 or topsheet 34 of the diaper. In a particular embodiment, the waist flap 90 is made from a material which is substantially liquid impermeable or which has been rendered substantially liquid impermeable to provide improved containment of the fecal material.

Accordingly, the different aspects of the present invention advantageously provide an absorbent article having improved containment and control of body exudates and, in particular, fecal material. The collection conduit of the present invention has the properties of compression resilience and flexibility to effectively collect fecal material from the skin of the wearer. As a result, such a collection conduit may reduce the amount of leaks from absorbent articles which are caused by fecal material sliding along the skin of the wearer and, in particular, along the skin of the wearer in the gluteal fold region between the buttocks of the wearer. The collection conduit also provides a transportation duct to transport the fecal material out of the narrow crotch portion and into the rear portion of the article or a centrally located void space in the article where the article is better able to contain and absorb it. As a result, absorbent articles made according to the present invention may have a reduced incidence of leaks in the crotch portion of the article.

Compression Resistance Test

This test is configured to measure the compression resistance of materials intended for use as the collection conduit according to the present invention. The compression resistance of the materials indicates the ability of the material to maintain it's interior void volume during use.

A sample of the material intended for use as the conduit is cut to a length of 5.0 inches (12.7 centimeters). A plate having a length of 5.0 inches (12.7 centimeters) and a width of 1.5 inches (3.8 centimeters) is placed on the conduit and the height of the conduit is measured and recorded as the original height. A weight of 4.66 pounds (2.11 kilograms) is then placed on the plate and the compressed height of the conduit is measured. The compression resistance value of the material sample is then obtained by dividing the compressed height by the original height and multiplying the result by 100 percent.

Flexibility Test

This test is configured to measure the flexibility of materials intended for use as the collection conduit according to the present invention. The flexibility of the materials indicates the ability of the material to conform to the wearer's body without causing irritation. A sample of the material intended for use as the conduit is cut to a length of 9.0 inches (22.9 centimeters). The sample is placed on a horizontal plate which has attached to one end thereof a decline plate which declines at an angle of 42 degrees from the horizontal plane. One end of the sample is aligned with the intersection of the horizontal plate and the decline plate. A force is then applied to the opposite end of the sample to move the sample at a rate of 1.27 centimeters per second over the decline plate. The sample is moved over the decline plate until the overhanging end of the sample bends and comes into contact with the decline plate. The distance which the sample traveled up until contact with the decline plate is then measured and recorded as the flexibility value for the sample.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. A disposable absorbent article which comprises a backsheet layer, an absorbent which is connected in superposed relation to said backsheet layer and a conduit means which is located on and connected to a bodyfacing surface and extends along a longitudinal centerline of said absorbent article for collecting and transporting fecal material and which is configured to maintain at least partial contact with a gluteal fold region between a wearer's buttocks when in use wherein said conduit means defines a compression resistance of at least about 25 percent as determined according to a Compression Resistance Test set forth herein.

2. An absorbent article according to claim 1 wherein said conduit means defines an internal void volume of at least about 5.0 cubic centimeters for containing said fecal material.

3. An absorbent article according to claim 1 wherein said conduit means defines an internal cross-sectional area of at least about 0.4 square centimeters.

4. An absorbent article according to claim 1 wherein said conduit means defines a length of at least about 5.0 centimeters.

5. An absorbent article according to claim 1 wherein said conduit means includes an exterior wall which defines an internal duct and at least one opening through said exterior wall into said internal duct for collecting and transporting said fecal material.

6. An absorbent article according to claim 5 wherein said at least one opening is selectively located along a portion of said conduit means which is located in a target zone of said article and which is configured to remain substantially free of contact with said bodyfacing surface of said absorbent article in use to collect said fecal material from said wearer.

7. An absorbent article according to claim 5 wherein said conduit means defines from 1 to about 10 openings through said exterior wall into said internal duct for collecting and transporting said fecal material.

8. An absorbent article according to claim 7 wherein each of said openings defines an area of at least about 0.8 square centimeters.

9. An absorbent article according to claim 5 wherein said conduit means further defines a plurality of holes through said exterior wall into said internal duct at locations which are at least partially in contact with said bodyfacing surface of said absorbent article for allowing liquid portions of said fecal material to pass from said internal duct into an absorbent body of said absorbent article.

10. An absorbent article according to claim 5 wherein said internal duct extends along a length of said conduit means and defines an average cross sectional area of at least about 0.4 square centimeters.

11. An absorbent article according to claim 5 wherein said internal duct extends along a length of said conduit means and defines an average cross sectional area of at least about 1.0 square centimeters.

12. An absorbent article according to claim 1 wherein said conduit means includes an exterior wall which defines an internal duct wherein at least about 25 percent of said exterior wall remains open in a target zone to collect and transport said fecal material into said internal duct.

13. An absorbent article according to claim 12 wherein a portion of said exterior wall which remains open defines an open area of at least about 5.0 square centimeters.

14. An absorbent article according to claim 1 wherein said conduit means comprises a spring coil having an inside diameter of at least about 0.5 centimeters and a spacing between each coil for collecting and transporting said fecal material.

15. An absorbent article according to claim 1 wherein said conduit means comprises a tube having a plurality of holes therethrough.

16. An absorbent article according to claim 1 wherein said conduit means defines a flexibility of less than about 20 centimeters as determined according to a Flexibility Test set forth herein.

17. An absorbent article having a front waist section, a rear waist section, an intermediate section which interconnects said front and rear waist sections, a pair of longitudinally opposed end edges, and a pair of laterally opposed side edges, said article comprising:

a) a backsheet layer;
b) a liquid permeable topsheet layer which is connected in superposed relation to said backsheet layer;
c) an absorbent body which is located between said topsheet layer and said backsheet layer; and
d) a collection conduit which extends along a longitudinal centerline of said absorbent article and which includes an exterior wall which defines an internal duct for collecting and transporting fecal material wherein said conduit means defines a compression resistance of at least about 25 percent as determined according to a Compression Resistance Test set forth herein.

18. An absorbent article according to claim 17 wherein said internal duct defines a void volume of at least about 5.0 cubic centimeters for containing said fecal material.

19. An absorbent article according to claim 17 wherein said collection conduit defines a length of from about 10 to about 80 percent of a length of said article.

20. An absorbent article according to claim 19 wherein said collection conduit defines opposed ends wherein a first one of said ends is located in said intermediate section of said absorbent article and a second one of said ends is located in said rear waist section of said absorbent article.

21. An absorbent article according to claim 20 wherein said first end is located from about 0 to about 5.0 centimeters form a lateral centerline of said absorbent article towards said front waist section of said absorbent article.

22. An absorbent article according to claim 17 wherein at least about 25 percent of said exterior wall in a target zone of said article remains open to collect and transport said fecal material into said internal duct.

23. An absorbent article according to claim 22 wherein a portion of said exterior wall which remains open defines an open area of at least about 5.0 square centimeters.

24. An absorbent article according to claim 17 wherein said collection conduit comprises a spring coil having an inside diameter of at least about 0.5 centimeters and a spacing between each coil for collecting and transporting said fecal material.

25. An absorbent article according to claim 17 wherein said collection conduit comprises a tube having a plurality of holes therethrough.

26. An absorbent article according to claim 17 wherein said collection conduit defines a flexibility of less than about 20 centimeters as determined according to a Flexibility Test set forth herein.

27. An absorbent article according to claim 17 and further comprising a waist flap which is located in said rear waist section of said absorbent article and which defines an attached edge which is attached to said end edge and said side edges of said absorbent article in said rear waist section and a free edge which extends inwardly from said end edge towards said intermediate section and which remains at least partially unattached to said topsheet of said absorbent article to provide a pocket to contain body exudates.

28. An absorbent article according to claim 27 wherein said waist flap extends inwardly over an end of said collection conduit.

29. An absorbent article having a front waist section, a rear waist section, an intermediate section which interconnects said front and rear waist sections, a pair of longitudinally opposed end edges, and a pair of laterally opposed side edges, said article comprising:
 a) a backsheet layer;
 b) a liquid permeable topsheet layer which is connected in superposed relation to said backsheet layer;
 c) an absorbent body which is located between said topsheet layer and said backsheet layer; and
 d) a spiral coil which extends along a longitudinal centerline of said absorbent article and which defines an interior void volume of at least about 5.0 cubic centimeters and a compression resistance of at least about 25 percent as determined according to a Compression Resistance Test set forth herein for collecting and transporting fecal material.

30. An absorbent article according to claim 29 wherein said interior void volume is at least about 15.0 cubic centimeters.

31. An absorbent article according to claim 29 wherein said spiral coil defines a compression resistance of at least about 50 percent.

32. An absorbent article according to claim 29 wherein said spiral coil defines a flexibility of less than about 20 centimeters as determined according to a Flexibility Test set forth herein.

33. An absorbent article according to claim 29 wherein said spiral coil includes a nonwoven material covering at least a portion of an outer surface of said spiral coil which is configured to be in contact with a wearer's skin in use.

34. An absorbent article according to claim 29 wherein said spiral coil defines an inner surface having a coefficient of friction of no more than about 1.0.

35. An absorbent article according to claim 29 wherein said spiral coil defines a coil width of from about 0.2 to about 0.5 centimeters and a spacing width between said coils of from about 0.3 to about 1.5 centimeters.

36. An absorbent article according to claim 29 wherein said spiral coil defines an inside diameter of at least about 0.5 centimeters.

37. An absorbent article according to claim 29 wherein said spiral coil includes an exterior wall which defines said internal void volume wherein at least about 25 percent of said exterior wall in a target zone of said article remains open to collect and transport said fecal material into said internal void volume.

38. An absorbent article according to claim 37 wherein said exterior wall which remains open defines an open area of at least about 5 square centimeters.

* * * * *